United States Patent
Schwager

(10) Patent No.: US 9,279,779 B2
(45) Date of Patent: Mar. 8, 2016

(54) METHOD FOR IDENTIFYING A CRYSTALLOGRAPHIC CANDIDATE PHASE OF A CRYSTAL

(71) Applicant: Bruker Nano GmbH, Berlin (DE)

(72) Inventor: Thomas Schwager, Berlin (DE)

(73) Assignee: BRUKER NANO GMBH, Berlin (DE)

( * ) Notice: Subject to any disclaimer, the term of this patent is extended or adjusted under 35 U.S.C. 154(b) by 0 days.

(21) Appl. No.: 14/621,580

(22) Filed: Feb. 13, 2015

(65) Prior Publication Data

US 2015/0233843 A1      Aug. 20, 2015

(30) Foreign Application Priority Data

Feb. 20, 2014   (DE) .......................... 10 2014 203 090

(51) Int. Cl.
*H01J 37/26* (2006.01)
*G01N 23/207* (2006.01)
*G01N 23/203* (2006.01)

(52) U.S. Cl.
CPC ............ *G01N 23/207* (2013.01); *G01N 23/203* (2013.01)

(58) Field of Classification Search
USPC ................. 250/305, 306, 307, 309, 310, 311; 702/22, 27, 28, 30
See application file for complete search history.

(56) References Cited

U.S. PATENT DOCUMENTS

| 2004/0011958 A1* | 1/2004 | Wright et al. ................. 250/307 |
| 2011/0220796 A1* | 9/2011 | Nicolopoulos et al. ....... 250/307 |

* cited by examiner

*Primary Examiner* — Nicole Ippolito
(74) *Attorney, Agent, or Firm* — Novak Druce Connolly Bove + Quigg LLP

(57) ABSTRACT

According to the invention a method is provided for identifying a crystallographic candidate phase of a crystal in an EBSD diffraction pattern, which includes the following steps: Sorting and indexing of the bands of the diffraction pattern in order of decreasing intensity. Providing of indices of the diffraction bands of candidate phases, which are to be expected as a result of the EBSD pattern acquisition, in a database, wherein all the indices provided can, in each case, be assigned to a candidate phase. Identification of the expected bands with the bands measured in the diffraction pattern for each candidate phase. Comparison of the intensities of bands of the measured diffraction pattern with intensities which were predicted for the diffraction bands of the candidate phases, which are to be expected as a result of the EBSD pattern acquisition, the indices of said candidate phases being stored in the database. In addition, a corresponding computer program and a computer-readable storage medium are provided, on which a computer program according to the invention is stored.

7 Claims, No Drawings

METHOD FOR IDENTIFYING A CRYSTALLOGRAPHIC CANDIDATE PHASE OF A CRYSTAL

CROSS-REFERENCE TO RELATED APPLICATIONS

This application claims priority to German Application No. 10 2014 203 090.0, filed Feb. 20, 2014, all of which is hereby incorporated herein by reference in its entirety.

This invention relates to a method for identifying a crystallographic candidate phase of a crystal. The invention also relates to an associated computer program and a computer-readable storage medium.

PRIOR ART

Electron backscatter diffraction (EBSD) is a crystallographic technique used to analyze the structure of crystals. An electron beam is scattered on the atoms of the specimen to be measured and the resulting diffraction pattern is recorded. The problem with distinguishing between similar crystallographic phases (candidate phases) is frequently that two or more candidate phases indicate a pattern, i.e. the characteristic diffraction pattern of a crystal, equally well. Therefore, the solution for austenite (FCC iron) and ferrite (BCC iron) shown in Table 1 can be found, for example, in one pattern.

TABLE 1

Indexing solution for FCC and BCC iron

| Band | FCC-Index | BCC-Index |
|---|---|---|
| 1 | (220) | (110) |
| 2 | ($\bar{2}$20) | ($\bar{1}$10) |
| 3 | (200) | (200) |
| 4 | (242) | (121) |
| 5 | (42$\bar{2}$) | (21$\bar{1}$) |
| 6 | (422) | (211) |
| 7 | ($\bar{2}$42) | ($\bar{1}$21) |
| 8 | (111) | (222) |

The bands are sorted here roughly in accordance with the measured intensity. The band numbered 1 therefore has the greatest intensity, while the band numbered 8 has the lowest intensity. Obviously, both indexing solutions describe the pattern equally well. The number of bands is the same, and the band locations are the same. Only the width of the predicted bands is different. Since the bandwidth is difficult to measure, it is very complicated to make a reliable distinction based on bandwidths during the identification.

It is therefore an object of this invention to provide a method which makes it possible for a crystallographic candidate phase of a crystal to be identified more clearly and more reliably.

DISCLOSURE OF THE INVENTION

A method for identifying a crystallographic candidate phase of a crystal in an EBSD diffraction pattern is provided according to the invention, which includes the following steps: Sorting and indexing of the bands of the diffraction pattern in order of decreasing intensity. Providing of indices of the diffraction bands of candidate phases, which are to be expected as a result of the EBSD pattern acquisition, in a database, wherein all the indices provided can, in each case, be assigned to a candidate phase. Identification of the expected bands with the bands measured in the diffraction pattern for each candidate phase. Comparison of the intensities of bands of the measured diffraction pattern with intensities which were predicted for the diffraction bands of the candidate phases, which are to be expected as a result of the EBSD pattern acquisition, the indices of said candidate phases being stored in the database.

The advantage of the method according to the invention is that a clear and reliable identification of phases and/or candidate phases in a simple manner is made possible with the same method. The term 'EBSD system' denotes a system which is able to acquire and evaluate electron backscatter diffraction patterns. The EBSD system can, for example, be realized in a scanning electron microscope or in a transmission electron microscope or in any other system as well. In addition, the term 'diffraction pattern' denotes the electron backscatter pattern which is also known as a Kikuchi pattern.

The measurement respectively determination of the intensities of Kikuchi bands has long been known from the prior art and is mainly carried out as part of a pattern analysis, for example, as indicated below.

First of all, diffraction patterns for measuring band locations are subjected to a Radon or Hough transformation following a few standard processing steps (background subtraction, contrast enhancement, etc.). Linear features in the diffraction pattern are converted into bright sharp peaks in the transformed pattern. Even very wide diffraction bands can be evaluated in this way. Instead of isolated bright points in the transformed pattern, small-scale, bright structures (also referred to as 'butterflies' in some of the following sources) are obtained in the case of Hough transformation-based approaches. The intensities of these points and/or these structures in the transformed image, the so-called Hough image, are regularly used as a rough measure of the intensity of the Kikuchi bands. In the further course of the pattern analysis, the brightest peaks in the Hough image are observed and the associated band locations resulting from the position of the peak in the Hough image are determined. Since the brightest peaks are started with, the intensities of the measured diffraction bands are sorted roughly.

This is described, for example, in the work of Niels Christian Krieger Lassen, "Automated Determination of Crystal Orientations from Electron Backscattering Patterns", IMM-DTU, Technical University of Denmark, 1994, page 98. This explicitly mentions that the height of the Hough peaks can be used as a measure of the intensity of the individual diffraction bands.

Other possible ways of determining the intensity of diffraction bands can be inferred, for example, from the article by Robert A. Schwarzer, "Automated Crystal Orientation Measurements by backscatter Kikuchi diffraction", Dept. of Physics, Clausthal University of Technology, Germany, page 166.

The method for pattern analysis described above is also explained in more detail in the article by N. C. Krieger Lassen, "Automatic high-precision measurements of the location and width of Kikuchi bands in electron backscatter diffraction patterns", Journal of Microscopy, Vol. 190, Pt 3, June 1998, pages 375-391, and in the article by Robert A. Schwarzer and Johann Sukkau, "Automated evaluation of Kikuchi Patterns by Means of Radon and Fast Fourier Transformation, and Verification by an Artificial Neural Network", Advanced Engineering Materials, 5, No. 8, 2003, pages 601-603.

The indices of the diffraction bands of candidate phases, which are to be expected as a result of the EBSD pattern acquisition, are preferably provided in a database, from which a pre-selection is made by a user. In other words, a pre-analysis of the examined crystal is preferably carried out, for example by a user of the method, in order to identify possible crystallographic candidate phases. In addition, possible diffraction bands are preferably selected for each selected candidate phase and their indices are provided in a list. Furthermore, the predicted intensities are preferably theoretically determined from physical models and/or are predicted from data from other measuring methods with additional models. In addition, X-ray diffraction is preferably used in such measuring methods. In addition, it is preferred that not all of the bands are stored in the database, and/or that the indices of all bands are not stored in the database, but only one in each case from a group of symmetry-equivalent bands. The bands which are not stored are preferably generated with knowledge of the crystal symmetry.

Intensity ranks are preferably assigned to the provided indices of the expected diffraction patterns as a result of the EBSD pattern acquisition, in each case, according to the predicted intensity for the respective diffraction band, wherein the highest intensity rank is assigned to the index of the diffraction band, for which the greatest intensity is predicted. Since the bands of a diffraction pattern are determined, sorted by the EBSD system in the order of their intensity in the diffraction pattern, the comparability of these determined bands can be significantly simplified with the expected diffraction bands of candidate phases, the indices of which are stored in the database, by means of the assignment of said intensity ranks to the indices of a respective candidate phase. The second highest intensity rank is preferably assigned to the index of the diffraction band of the second greatest intensity stored in the database, and so on. The same intensity ranks are preferably assigned to the indices of diffraction bands of the same intensity stored in the database.

The indices of the bands of the measured diffraction pattern are preferably compared with the indices of the expected diffraction bands of the candidate phases as a result of the EBSD pattern acquisition, which are stored in the database, with respect to their intensity, in that those indices stored in the database, each of which can be assigned to a candidate phase, are arranged for each candidate phase according to the order of the determined indices, and the intensity ranks assigned to the indices stored in the database are used for the comparison. In such an embodiment of the method, the indices of the diffraction bands of the possible candidate phases for the comparison and/or for the identification stored in the database are arranged with respect to their orientation in the order in which the indices of the bands of the diffraction pattern of the crystallographic candidate phase to be identified by means of the EBSD system are determined and/or emitted. It is subsequently very easy to establish, based on an observation of the order of the intensity ranks assigned to the indices of a candidate phase, whether the candidate phase is the crystallographic candidate phase to be identified with the EBSD system.

In a preferred embodiment, the comparison with the indices stored in the database is carried out in that the indices stored in the database, which are arranged in the order of the determined bands, each of which indices can be assigned to a candidate phase, are permutated with each other in pairs, such that the intensity ranks assigned to the indices of the candidate phase are sorted in descending order, wherein the highest intensity rank constitutes the first value in the intensity ranking, and the number of permutations of consecutive indices required to produce this intensity ranking is recorded. Only permutations of neighboring indices are permitted. Only successive indices can therefore be permutated with each other in each case. In other words, the indices stored in the database are sorted for each candidate phase according to their intensity ranks, wherein the index of the diffraction band of the highest intensity is in first place and the index of the diffraction band of the lowest intensity is in last place. The number of permutations of the indices stored in the database required to produce this intensity ranking is recorded as a measure of quality, referred to as the rank score, wherein the rank score of a candidate phase always corresponds to the lowest number of permutations which are required for the indices of a candidate phase stored in the database, in order to organize the same according to the intensity ranking. Using this rank score it can very easily be determined whether a crystallographic candidate phase to be identified can be identified as a candidate phase, the indices of which are stored in the database. Alternatively, the intensity ranks of the associated indices, in each case, can also only be permutated and the number of permutations in pairs in each case can be recorded as a rank score according to the above embodiment.

The indices of the candidate phase to be identified are preferably compared with the indices provided in the database of the expected diffraction bands of at least two candidate phases as a result of the EBSD pattern acquisition, which candidate phases indicate the same bands, and the candidate phase with the lowest number of required permutations with the candidate phase to be identified is identified. If the number of permutations required to produce the intensity ranking in the case of a candidate phase, the indices of which are stored in the database, is very low or zero, then it is very probable that this candidate phase is the candidate phase to be identified, since the intensities of the bands in the diffraction pattern of this candidate phase are very consistent with the predicted intensities of the bands of the candidate phase to be identified. The method according to the invention therefore makes it possible to clearly identify a candidate phase.

In addition, a computer program is provided, which makes it possible for a data processing system to carry out the method according to the invention, as soon as the computer program is loaded into the memory of the data processing system. It is possible to have the method carried out by a computer having such a computer program, which saves time and money, and which, in addition, allows the method to be carried out more efficiently than if it were carried out by human hand.

In addition, a computer-readable storage medium is provided, on which a computer program is stored, which makes it possible for a data processing system to carry out the method according to the invention as soon as the computer program is loaded into the memory of the data processing system. In such an embodiment, the computer program according to the invention can, for example, access the computer-readable storage medium, on which a database can be stored in addition to the program, which includes a large number of indices associated with the diffraction bands of candidate phases, together with the intensity ranks associated therewith.

Additional advantageous further developments of the invention are indicated in the dependent claims or can be inferred from the following description.

EMBODIMENTS OF THE INVENTION

An embodiment example of a method according to the invention will be described below by means of an example, in which a crystallographic candidate phase to be identified is to be identified as either austenite, i.e. FCC iron, or as ferrite, i.e. BCC iron. The specimen examined in this embodiment example is, purely by way of example, ferrite. For the purposes of identifying the specimen phase, the diffraction pattern is generated by irradiating the specimen with an electron beam by means of an EBSD system. The diffraction pattern contains characteristic bands, the location of which is measured. The measured bands are indicated for each of the two candidate phases, i.e. the Miller indices of the lattice planes, which generate the bands, are determined. The indices are different for both candidate phases. The indices are emitted, sorted in the order R of the measured band intensities, starting with the band of highest intensity. The EBSD system is realized in this embodiment example, purely by way of an example, in a scanning electron microscope. However, it can also be realized in another system or as a stand-alone, independent system. The following table 2 shows the result of the indexing of the diffraction pattern by means of the EBSD system, in which 8 bands have been identified, which, as mentioned above, have been determined, sorted by the EBSD system in the diffraction pattern in an order R according to their intensity. While band 1 was the brightest in the diffraction pattern, band 8 was the darkest of the bands measured in the diffraction pattern. Notwithstanding this example, there can also be many more bands in the diffraction pattern.

TABLE 2

Results of the evaluation of the diffraction pattern with the ferrite candidate phase selected by way of an example.

| Band | Ferrit | |
|---|---|---|
| 1 | (110) | |
| 2 | ($\bar{1}$10) | |
| 3 | (200) | |
| 4 | (121) | R |
| 5 | (21$\bar{1}$) | |
| 6 | (211) | |
| 7 | ($\bar{1}$21) | |
| 8 | (222) | |

| Band | Ferrite |
|---|---|

As part of the method according to the invention, the 8 bands of the diffraction pattern are therefore sorted and indexed in the order R of decreasing intensity. In addition, indices of diffraction patterns, which are to be expected as a result of the EBSD pattern acquisition, of possible candidate phases for the identification of the examined candidate phase are provided in a database. The indices of the diffraction bands of the possible candidate phases are therefore stored in a database, wherein all indices can, in each case, be assigned to a possible candidate phase. The possible diffraction bands of candidate phases are thus selected in this embodiment example of the method, purely by way of an example, by a user who is carrying out an analysis of the examined crystal. In this embodiment example, a prediction is made of the intensities and/or intensity values, which the respective diffraction band would have in a diffraction pattern during an EBSD examination, for the expected diffraction bands, the indices of which are stored in the database. The predicted intensities and/or intensity values are thus assigned to the associated indices, in each case, of the expected diffraction bands. The intensities are predicted, purely by way of example, in this embodiment using known values and/or values indicated in the literature. In other embodiment examples, the intensities and/or intensity values used for the prediction are theoretically determined from physical models. In other embodiment examples of the method according to the invention, the intensities and/or intensity values may also only be predicted approximately. In this embodiment example, intensity ranks are assigned to the indices stored in the database according to the intensity predicted, in each case, for an associated diffraction band. Intensity ranks are therefore assigned to the indices in this embodiment example, in each case, according to the predicted intensity of the diffraction band associated, in each case, with the indices within the diffraction pattern of the candidate phase, to which the respective indices can be assigned. The highest intensity rank is assigned to the index of the expected diffraction band of the greatest intensity. In the case of the candidate phase of FCC iron, the {111} bands are the brightest bands. The highest intensity rank "1" is therefore assigned to them. The {200}, {220}, {311}, {331}, {420} and {422} bands then follow. Higher-order bands with the same location as bands which have already been observed are not considered. The lowest intensity rank "7" is assigned to the {422} bands. The intensity ranking for the candidate phase of the BCC iron is {110}, {200}, {211}, {310}, {222} and {321}. Whilst the {110} bands are the brightest bands, to which the intensity rank "1" is therefore assigned, the {321} bands are the bands of the lowest intensity, which are therefore given the intensity rank "6". The same intensity ranks are assigned to bands of comparable intensity in this example.

In this embodiment example, the predicted intensities of the diffraction bands of the indices stored in the database are compared with those measured for the diffraction pattern of the examined candidate phase. To this end, the intensity rank resulting from the prediction of the intensity is noted for each band index, which is shown in Table 3. Like the specific band index, the intensity rank is also specific to the observed candidate phase. In this embodiment example of the method, those indices stored in the database, each of which can be assigned to a candidate phase, are arranged for each candidate phase according to the order R of the determined indices of the examined candidate phase, which also happened in Table 3. The arrangement is carried out in this embodiment example, purely by way of an example, with respect to the orientation of the expected diffraction bands which can be assigned to the indices, in the respective diffraction pattern of a candidate phase, so that similarly oriented diffraction bands are located in a row. Furthermore, the indices are numbered according to the respective associated band number.

TABLE 3

| Band | FCC-Index | Intensitätsrang$_{FCC}$ | BCC-Index | Intensitätsrang$_{BCC}$ |
|---|---|---|---|---|
| 1 | (220) | 3 | (110) | 1 |
| 2 | ($\bar{2}$20) | 3 | ($\bar{1}$10) | 1 |
| 3 | (200) | 2 | (200) | 2 |
| 4 | (242) | 7 | (121) | 3 |
| 5 | (42$\bar{2}$) | 7 | (21$\bar{1}$) | 3 |
| 6 | (422) | 7 | (211) | 3 |
| 7 | ($\bar{2}$42) | 7 | ($\bar{1}$21) | 3 |
| 8 | (111) | 1 | (222) | 5 |

| Band | FCC index | Intensity rank$_{FCC}$ | BCC index | Intensity rank$_{BCC}$ |

The indices of the candidate phases are therefore organized and numbered according to the order R. The indices of diffraction bands of the same location are therefore located at the same place, across the phases, within the order of their respective associated indices and bear the same band number. In the case of a suitable candidate phase, the intensity ranks are sorted by the band number in ascending order. High-intensity bands have been suitably predicted with a high intensity, low-intensity bands have been suitably predicted with a low intensity. In the example, the ferrite candidate phase, i.e. BCC iron, the indices of which are listed in the column with the "BCC Index" heading, predicts the correct intensity ranking.

The intensity ranking of the respective candidate phases is evaluated in that indices of the candidate phase arranged successively above one another and/or below one another are permutated with one another in pairs, until the intensity ranks assigned to the indices of the candidate phase are sorted in descending intensity ranking. The highest intensity rank, which is identified in this embodiment example in Table 3 with a "1", constitutes the first value in descending intensity ranking. The number of permutations of the indices among themselves required to produce this descending intensity ranking, which is referred to here as the rank score, is recorded.

In this embodiment example that candidate phase with the lowest number of necessary permutations, which therefore has the lowest rank score, is always identified as the candidate phase to be identified. In this embodiment example nine permutations are required for the candidate phase of the FCC iron, in order to produce the specified descending intensity ranking by means of the intensities of the bands of the diffraction pattern. The rank score of the candidate phase of FCC iron is therefore "9". The first step of permutation could, for example, be the permutation of the indices (−242) and (111). A further six permutations are needed to locate the index of the eighth band (111) in first place. Thereafter, a further two permutations are necessary to locate the band (200) in second place. However, no permutation is to be carried out with the candidate phase of BCC iron, since the intensity ranks are already arranged in descending intensity ranking. The rank score of the reference candidate phase of BCC iron is therefore "0". The candidate phase to be identified is therefore identified as BCC iron.

In this embodiment example the candidate phase to be identified is compared, for ease of understanding, with the indices of diffraction bands of only two candidate phases. However, methods according to the invention can also be carried out, in which a candidate phase to be identified is compared with the indices of a wide variety of candidate phases, for example with more than a hundred or an even larger number of candidate phases.

The invention claimed is:

1. A method for identifying a crystallographic candidate phase of a crystal in an EBSD diffraction pattern, comprising the steps of:
 (i) Sorting and indexing of the bands of the diffraction pattern in order (R) of decreasing intensity;
 (ii) Providing of indices of the diffraction bands of candidate phases, which are to be expected as a result of the EBSD pattern acquisition, in a database, wherein all the indices provided can, in each case, be assigned to a candidate phase;
 (iii) Identification of the expected bands with the bands measured in the diffraction pattern for each candidate phase; and
 (iv) Comparison of the intensities of bands of the measured diffraction pattern with intensities which were predicted for the diffraction bands of the candidate phases, which are to be expected as a result of the EBSD pattern acquisition, the indices of said candidate phases being stored in the database.

2. The method according to claim 1, wherein intensity ranks are, in each case, assigned to the provided indices of the expected diffraction bands as a result of the EBSD pattern acquisition according to the intensity predicted for the respective diffraction band, wherein the highest intensity rank is assigned to the index of the diffraction band for which the greatest intensity is predicted.

3. The method according to claim 2, wherein the indices of the bands of the measured diffraction pattern are compared with the indices of the expected diffraction bands of the candidate phases as a result of the EBSD pattern acquisition, which are stored in the database, in terms of their intensity, in that those indices stored in the database, each of which can be assigned to a candidate phase, are arranged for each candidate phase according to the order (R) of the determined indices, and the intensity ranks assigned to the indices stored in the database are used for comparison.

4. The method according to claim 3, wherein the comparison with the indices stored in the database is carried out in that the indices stored in the database and arranged in the order (R) of the determined bands, each of which can be assigned to a candidate phase, are permutated with one another in pairs such that the intensity ranks assigned to the indices of the candidate phase are sorted in descending order, wherein the highest intensity rank constitutes the first value in the intensity ranking, and the number of permutations of consecutive indices required to produce this intensity ranking is recorded.

5. The method according to claim 4, wherein the indices of the candidate phase to be identified are compared with the indices of the expected diffraction bands of at least two candidate phases as a result of the EBSD pattern acquisition, which are provided in the database, which candidate phases indicate the same bands, and the candidate phase is identified with the lowest number of required permutations with the candidate phase to be identified.

6. A computer program which makes it possible for a data processing system to carry out the method according to claim 1, as soon as the computer program is loaded into the memory of the data processing system.

7. A computer-readable storage medium on which a computer program according to claim 6 is stored.

* * * * *